US008829928B2

(12) United States Patent
Gonzalez et al.

(10) Patent No.: US 8,829,928 B2
(45) Date of Patent: Sep. 9, 2014

(54) METHODS AND DEVICES FOR ACQUIRING AN OIL SAMPLE AND MONITORING THE QUALITY THEREOF

(75) Inventors: Bernard A. Gonzalez, Saint Paul, MN (US); Abolghassem B. Mahmoodi, Saint Paul, MN (US); Steven Y. Yu, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 558 days.

(21) Appl. No.: 13/227,702

(22) Filed: Sep. 8, 2011

(65) Prior Publication Data

US 2012/0062251 A1    Mar. 15, 2012

Related U.S. Application Data

(60) Provisional application No. 61/382,553, filed on Sep. 14, 2010.

(51) Int. Cl.
*G01R 27/26* (2006.01)
*G01N 27/22* (2006.01)
*G01N 1/12* (2006.01)
*G01N 33/03* (2006.01)

(52) U.S. Cl.
CPC ............... *G01N 1/12* (2013.01); *G01N 27/226* (2013.01); *G01N 33/03* (2013.01)
USPC .............................. 324/686; 324/658; 324/663

(58) Field of Classification Search
CPC .............................. G01R 27/2605; G01D 5/24
USPC ............................................... 324/658–690
See application file for complete search history.

(56) References Cited

U.S. PATENT DOCUMENTS

| 6,469,521 | B1 | 10/2002 | Klun |
| 6,822,461 | B2 | 11/2004 | Klun |
| 6,853,203 | B2 | 2/2005 | Beylich |
| 7,389,689 | B2 | 6/2008 | Wargo |
| 7,504,836 | B2 * | 3/2009 | Chambon et al. ............. 324/698 |

(Continued)

FOREIGN PATENT DOCUMENTS

| DE | 199 47 669 | 5/2001 |
| DE | 200 23 542 | 1/2005 |

(Continued)

OTHER PUBLICATIONS

U.S. Appl. No. 12/991788, Yu, et al., filed May 12, 2009.

(Continued)

*Primary Examiner* — Melissa Koval
*Assistant Examiner* — Daniel Miller
(74) *Attorney, Agent, or Firm* — Kenneth B. Wood (57) ABSTRACT

Methods and devices are disclosed which can provide an indication of oil quality by measuring a capacitive property of the oil. The methods and/or devices may use a sample acquisition probe comprising a microvolume oil acquisition basin with a capacitive sensing element that is located on the floor of the basin and that is laterally bounded by an oleophilic wetting feature. The methods may involve immersing a sample acquisition probe at least partially into a supply of oil and withdrawing the probe from the supply of oil such that a microvolume oil sample is retained within a microvolume oil acquisition basin of the probe, and measuring a capacitive property of the microvolume oil sample with a capacitive sensing element that is located in the basin.

29 Claims, 4 Drawing Sheets

(56) References Cited

U.S. PATENT DOCUMENTS

| | | |
|---|---|---|
| 7,523,006 B2 | 4/2009 | Muhl |
| 7,523,646 B2 | 4/2009 | Klun |
| 7,652,490 B2 | 1/2010 | Muhl |
| 2003/0155935 A1 | 8/2003 | Klun |
| 2009/0153155 A1 | 6/2009 | Chambon |
| 2010/0172391 A1 | 7/2010 | Muhl |
| 2011/0043224 A1 | 2/2011 | Yu |

FOREIGN PATENT DOCUMENTS

| | | |
|---|---|---|
| DE | 10 2008 01447 | 9/2009 |
| JP | 2005-114567 | 4/2005 |
| WO | WO 03/060499 | 7/2003 |
| WO | WO 2005/098407 | 10/2005 |
| WO | WO 2005/098419 | 10/2005 |
| WO | WO 2007-075803 | 7/2007 |
| WO | WO 2009/015864 | 2/2009 |
| WO | WO 2009/140263 | 11/2009 |

OTHER PUBLICATIONS

International Search Report, PCT/US2011/050766, mailed Mar. 22, 2012, 4 pages.

* cited by examiner

METHODS AND DEVICES FOR ACQUIRING AN OIL SAMPLE AND MONITORING THE QUALITY THEREOF

CROSS REFERENCE TO RELATED APPLICATION

This application claims the benefit of U.S. Provisional Patent Application No. 61/382,553, filed Sep. 14, 2010, the disclosure of which is incorporated by reference herein in its entirety.

BACKGROUND

When oils (e.g. cooking oil, frying oil, fat, shortening, etc.) are exposed to high temperatures, oxidative reactions can take place that result in degradation of the oils. Thus, oil quality is often monitored e.g. in restaurant kitchens, so as to determine whether the oil is still suitable for use. A parameter often used to evaluate oil quality is the Total Polar (compound) Content of the oil. Various approaches (capacitive, spectroscopic, etc.) have been used for measuring the Total Polar Content of oils.

SUMMARY

Methods and devices are disclosed which can provide an indication of oil quality by measuring a capacitive property of the oil. The methods and/or devices may use a sample acquisition probe comprising a microvolume oil acquisition basin with a capacitive sensing element that is located on the floor of the basin and that is laterally bounded by an oleophilic wetting feature. The methods may involve immersing a sample acquisition probe at least partially into a supply of oil and withdrawing the probe from the supply of oil such that a microvolume oil sample is retained within a microvolume oil acquisition basin of the probe, and measuring a capacitive property of the microvolume oil sample with a capacitive sensing element that is located in the basin.

In one aspect, herein is disclosed a device for acquiring a microvolume oil sample from a supply of oil and for measuring a capacitive property of the microvolume oil sample, comprising: a sample acquisition probe comprising a microvolume oil acquisition basin with a capacitive sensing element located on the floor of the basin and with a fluorinated barrier coating located atop the basin floor and the capacitive sensing element thereon; and wherein the capacitive sensing element and the fluorinated barrier coating atop the capacitive sensing element are laterally bounded by an oleophilic wetting feature.

In another aspect, herein is disclosed a method of measuring a capacitive property of a microvolume oil sample, comprising: providing a capacitive sensing element located on the floor of a microvolume oil acquisition basin of a sample acquisition probe; immersing the sample acquisition probe at least partially into a supply of oil and withdrawing the probe from the supply of oil such that a microvolume oil sample is retained within the oil acquisition basin in such manner as to completely cover the capacitive sensing element; and, using the capacitive sensing element to measure a capacitive property of the microvolume oil sample.

BRIEF DESCRIPTION OF THE DRAWINGS

These and other features and aspects of the present description will be more fully understood from the following detailed description of exemplary embodiments. It should be understood that the foregoing generalized descriptions and the following detailed descriptions are exemplary and are not restrictive of the present description.

Like reference numbers in the various figures indicate like elements. Certain elements may be present in identical multiples; in such cases a only single representative element may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", bottom", "upper", "lower", "under", "over", "front", "back", "outward", "inward", "up" and "down", and "first" and "second" may be used in this disclosure, it should be understood that those terms are used in their relative sense only unless otherwise noted.

DETAILED DESCRIPTION

Figure 1:
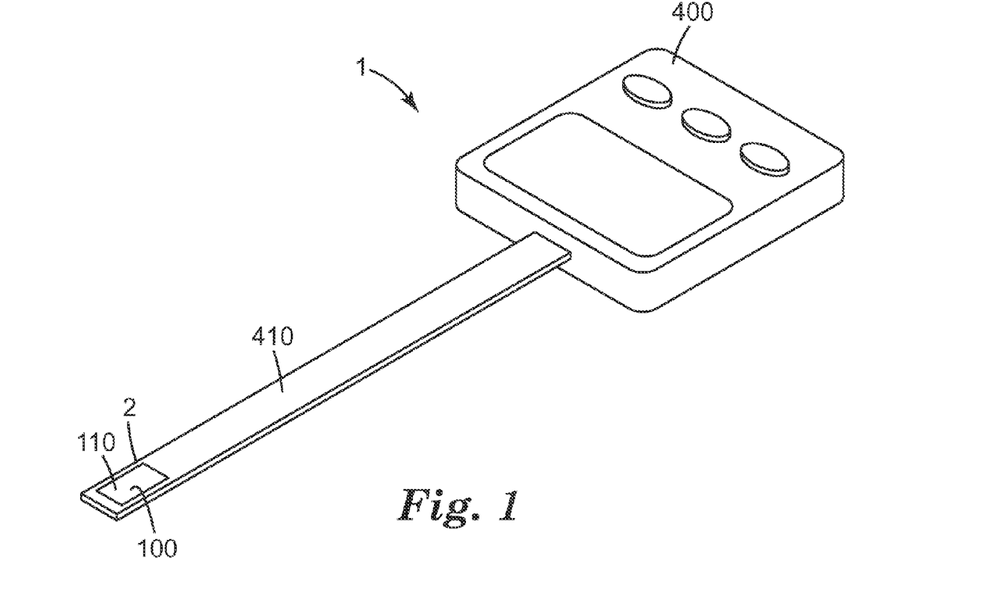
FIG. 1 is a perspective view of an exemplary oil quality monitoring device comprising a sample acquisition probe comprising a microvolume oil acquisition basin that comprises a capacitive sensing element with a fluorinated barrier coating.

FIG. 1 shows a perspective view of an exemplary oil quality measuring device 1 which may be used in monitoring the quality of a liquid oil, e.g. cooking oil, frying oil, etc., such as may be used in restaurants and the like. Device 1 comprises a control unit 400 which may contain electronic circuitry for signal processing, data handling, receiving of operator input, and so on. Device 1 further comprises sample acquisition probe 2 that comprises microvolume oil acquisition basin 100, which comprises capacitive sensing element 110. Capacitive sensing element 110 is operatively connected to control unit 400 so that it may be operated thereby, as may be achieved by any suitable mechanism, as discussed later
} herein. Sample acquisition probe 2 comprising microvolume oil acquisition basin 100 with capacitive sensing element 110 therein may be physically connected to control unit 400 e.g. by connecting member 410.

Figure 2:
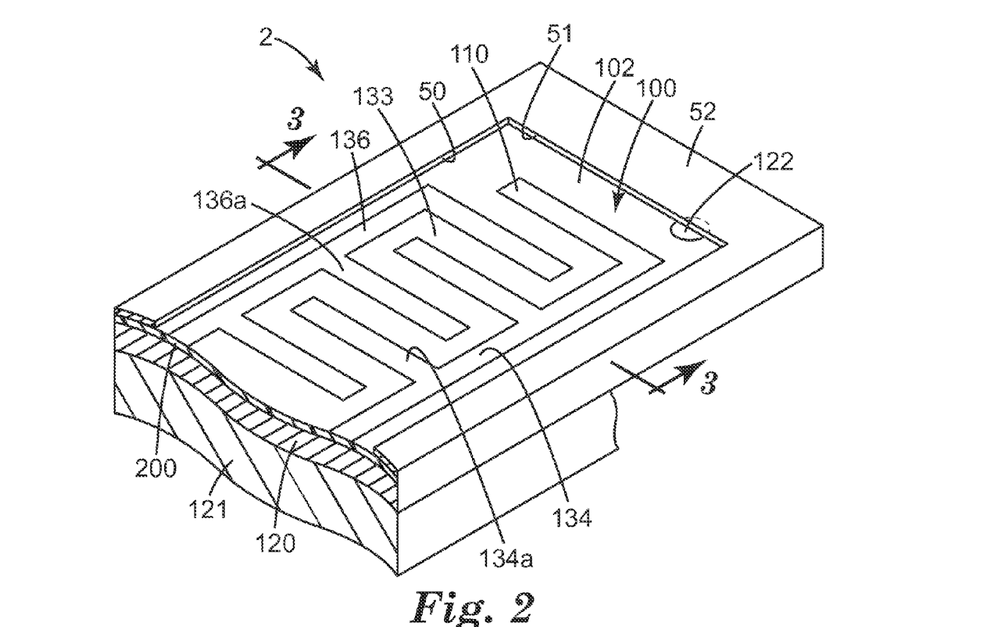
FIG. 2 is a perspective view of an exemplary microvolume oil acquisition basin comprising a capacitive sensing element with a fluorinated barrier coating.
Figure 3:
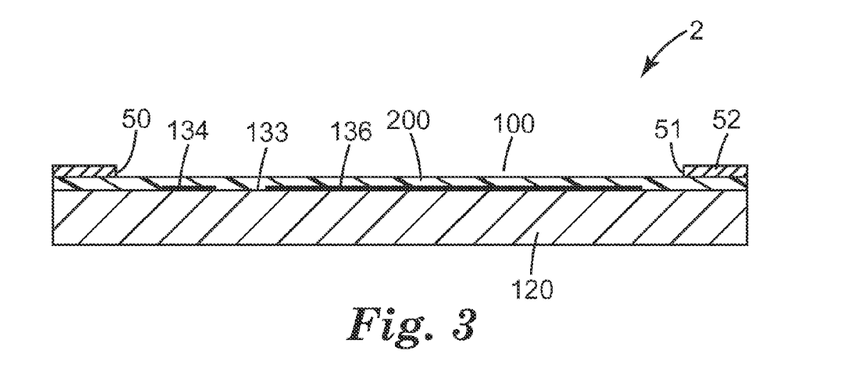
FIG. 3 is a cross sectional view of the microvolume oil acquisition basin of FIG. 2, taken along line 3-3 of FIG. 2.

FIG. 2 contains an enlarged perspective view of an exemplary sample acquisition probe 2 containing microvolume oil acquisition basin 100 with capacitive sensing element 110 therein. FIG. 3 shows a cross sectional view of probe 2 further illustrating microvolume oil acquisition basin 100. Microvolume oil acquisition basin 100 by definition has a nominal capacity of no more than 500 microliters, and may take the form of a generally shallow basin with a depth that is much less than the lateral dimensions of the basin and with an upward-facing opening so that a microvolume oil sample can be received into the basin. The upward-facing opening may be coextensive with the lateral dimensions of basin 100, as in the exemplary embodiment of FIG. 2. (In some embodiments, discussed later herein, the upward-facing opening may comprise an oil-spreading sheet through which oil may pass to reach basin 100). The floor 102 of basin 100 may be provided by a generally flat upper surface of substrate 120 (or of a layer upon substrate 120), bearing capacitive sensing element 110 and fluorinated barrier coating 200 thereupon. Capacitive sensing element 110 may take the form e.g. of a pair of electrically conductive pathways that together comprise capacitive electrodes, e.g., interdigitated electrodes 134 and 136. A capacitive property of an oil sample may be measured by way of electrodes 134 and 136 (e.g., by monitoring the effect of the oil on the capacitance, impedance, etc. of electrodes 134 and 136), and may then be correlated with the Total Polar Content of the oil sample, thus allowing the oil quality to be ascertained.

As used herein, the terms upward and upper means facing or oriented outward from basin 100 in a direction generally opposite substrate 120 (e.g., toward the top of FIG. 3); the terms downward and lower means facing or oriented outward from substrate 120 in a direction opposite basin 100 (e.g., toward the bottom of FIG. 3). The term lateral refers to directions generally parallel to the plane of substrate 120 and the plane of basin 100, and the term vertical refers to directions (upward and downward) generally normal to the plane of substrate 120 and basin 100. The term above means upward along the vertical direction. The term microvolume is defined as a volume of less than 500 microliters, as discussed in detail later herein.

Substrate 120 may be made of any suitable material that may carry electrical conductive pathways thereon without materially adversely affecting electrical measurements and that is sufficiently thermally stable to provide for the herein-disclosed uses. In particular, substrate 120 may be chosen to tolerate the temperatures of cooking oils (e.g., 150, 175, or 200° C. or more) For example, substrate 120 may be made ceramic-filled fluoropolymer, such as the product available from Arlon, Inc., Rancho Cucamonga, Calif., under the trade designation Isoclad. In some embodiments it may be desired to provide optional passive thermal mass element 121 located adjacent at least a portion of substrate 120 and in intimate thermal contact therewith (or in intimate thermal contact with a layer which is in intimate thermal contact with substrate 120). Thermal mass element 121 may provide a predetermined thermal mass which may affect the rate at which thermal mass element 121, and substrate 120 and capacitive sensing element 110 thereupon, heat up when placed into an oil supply, and/or the rate at which they, along with an acquired microvolume oil sample within basin 100, cool down after acquisition of the microvolume oil sample, as discussed later in detail.

Interdigitated electrode 134 and interdigitated electrode 136 are positioned on substrate 120 in spaced configuration so as to together comprise interdigitated capacitive sensing element 110, according to methods well known in the art. Interdigitated electrodes 134 and 136 may be made by coating portions of substrate 120 with conductive material to form a patterned continuous conductive trace (pathway) by any suitable process. The conductive material may be provided directly atop an exposed surface of the material of which substrate 120 is comprised; or, the conductive material may be provided atop an exposed surface of layer of material (e.g. a tie layer, primer layer, adhesion-promoting layer, etc.) present upon substrate 120. The (lateral) width, thickness (depth), pitch, etc. of the electrodes may be chosen as desired, as may gap (i.e., lateral space) 133 between adjacent portions of interdigitated fingers 134a and 136a of respective electrodes 134 and 136. While in the exemplary arrangement of FIG. 2 interdigitated electrodes 134 and 136 comprise rectilinear patterns (often called comb-style interdigitated patterns), other arrangements, such as interdigitated spiral patterns and the like, may be used. Interdigitated electrodes 134 and 136 may be connected by leads to contact pads (not shown in any figure) which are electrically connectable to control unit 400, which may include capacitance measuring circuitry, temperature measuring circuitry, control circuitry for operating the above-mentioned devices, for processing data received therefrom, for presenting the results of such processing to a user, for storing the data and/or results, for transmitting the data and/or results to a remote receiving location, and the like.

A temperature sensor 122 may be provided for monitoring the temperature of element 110 and/or of a microvolume oil sample within basin 100. In some embodiments, an active temperature control element (e.g., a powered heating block; not shown in any figure) may be provided, if it is desired to bring the oil sample and/or element 110 to a particular temperature for testing. In other embodiments, no active temperature control element is present with the capacitance measurement thus being performed with the microvolume oil sample at an uncontrolled temperature, as discussed in detail later herein.

Capacitive sensing element 110 comprises a fluorinated barrier coating 200 that covers interdigitated electrodes 134 and 136, and that additionally covers basin floor 102 (e.g., an upper surface of substrate 120 or of a layer upon substrate 120) in gaps 133 between electrodes 134 and 136. Thus, a microvolume oil sample that is acquired within basin 100 will reside on the outermost exposed surface of fluorinated barrier coating 200, as shown in the cross sectional view of FIG. 3. For optimum accuracy of the capacitive measurement, it may be desired that the acquired microvolume oil sample completely cover the entirety of capacitive sensing element 110 (e.g., the entirety of interdigitated electrodes 134 and 136 and gaps 133 therebetween, not necessarily including contact pads and connections thereto).

Fluorinated barrier coating 200 may provide significant advantages in durability, cleanability, etc., as discussed in detail in U.S. patent application Ser. No. 12/542,829, to Yu et. al. However, it has been discovered that fluorinated barrier coating 200 may present a problem in the sample acquisition format disclosed herein, in which a microvolume oil sample is acquired into relatively wide, shallow microvolume basin 100. Since fluorinated barrier coating 200 will likely be highly oleophobic, the acquired microvolume oil sample may tend to dewet from areas of coating 200 and/or to bead up preferentially in certain locations of basin 100. Such behavior may disadvantageously affect the accuracy and/or precision of measurements made using capacitive sensor 110. Accordingly, the methods and devices disclosed herein have been developed to enhance the functioning of microvolume oil sample acquisition devices and/or methods.

Accordingly, oleophilic wetting feature 50 may be provided within microvolume oil acquisition basin 100 of sample acquisition probe 2, as illustrated in a various exemplary embodiments in FIGS. 2-8. Oleophilic wetting feature 50 by definition laterally bounds (i.e., surrounds, encircles, etc., although not limited to a strictly circular, or even to a generally circular, configuration) capacitive sensing element 110 and comprises at least one surface that is contactable by a microvolume oil sample within basin 100 and that is nonfluorinated (defined herein as having a total fluorine content of less than 0.05 percent by weight) with a surface energy of at least 30 dynes/cm. Oleophilic wetting feature 50 may ensure that a microvolume oil sample 90, once acquired into basin 100, remains wetted over the entire area of the basin floor that contains capacitive sensing element 110, as shown in exemplary manner in FIG. 4. In some embodiments, oleophilic wetting feature 50 may define the lateral boundaries of microvolume oil acquisition basin; in other embodiments, oleophilic wetting feature 50 may be located laterally within boundaries of microvolume oil acquisition basin 100 that are provided by some other bounding feature or barrier (e.g., sidewall).

Figure 4:
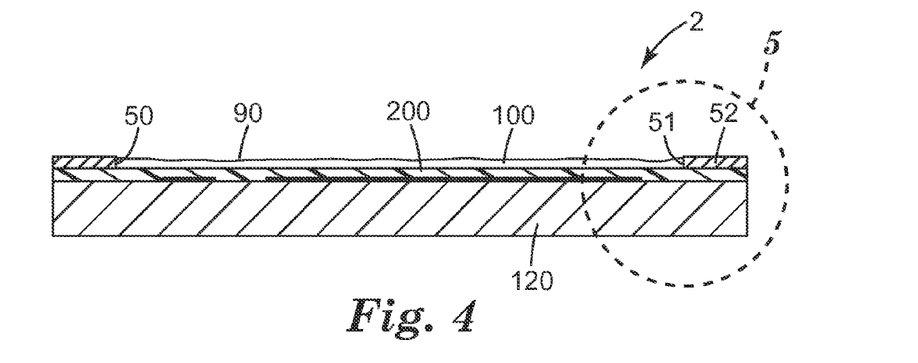
FIG. 4 is a cross sectional view of the microvolume oil acquisition basin of FIG. 3, with the basin comprising an oil sample.
Figure 5:
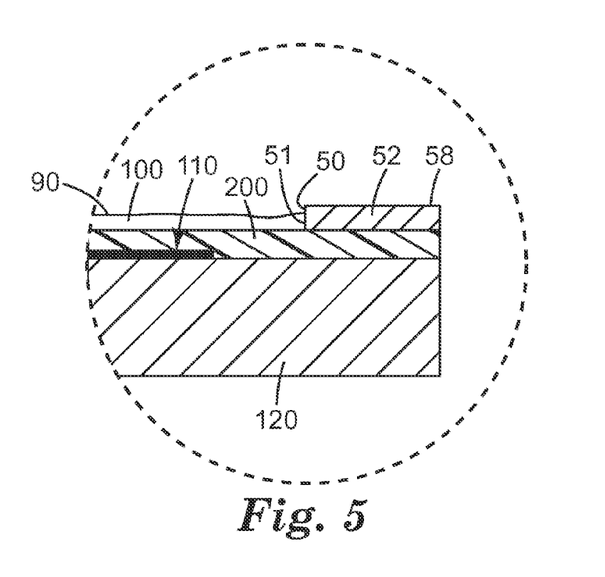
FIG. 5 is a partial cross sectional view of an exemplary microvolume oil acquisition basin comprising an exemplary oleophilic wetting feature.

Oleophilic wetting feature 50 may be chosen from a number of different designs. In FIGS. 2-4, and in magnified view in FIG. 5, is depicted an embodiment in which oleophilic wetting feature 50 comprises oleophilic edge 51 of layer 52 (which may be e.g. a strip, frame, partial frame, etc.). Layer 52 protrudes vertically above the plane of fluorinated coating 200; at least the laterally inward-facing face of edge 51 should be nonfluorinated with a surface energy of greater than 30 dyne/cm (with oleophilic being defined herein as having at least some exposed surface area that is nonfluorinated with a surface energy of greater than 30 dyne/cm). Any or all other surfaces of layer 52 (e.g., upper surface 58) may also be oleophilic, if desired. Layer 52 may be provided e.g. by depositing oleophilic material by any suitable method such as e.g. coating, vapor deposition, sputtering, etc., so as to form a layer at a desired location within basin 100 laterally outward of capacitive sensing element 110. Or, a pre-formed layer of material may be provided in a suitable format (e.g., as a strip) and positioned as desired within basin 100. In either case, layer 52 may be adhesive or may be non-adhesive, and may be attached in place by any suitable attachment mechanism. For example, layer 52 might comprise an adhesive surface (e.g., a pressure sensitive adhesive surface) so that it may be directly bonded to substrate 120 (or to a layer thereon); or, layer 52 might be nonadhesive but might be adhered to substrate 120 by a separate layer of adhesive, or by solvent bonding, or by any other suitable method. Layer 52 may comprise an exposed upper surface 58 (e.g., as in FIGS. 2-5); or, the upper surface of layer 52 may optionally be covered by a layer of some other material. However, oleophilic wetting feature 50 by definition does not encompass an edge 51 of an adhesive frame that is used to bond a filter material or an absorbent pad in proximity to basin 100.

Although shown in FIG. 2 as having generally straight sections that meet at right angles, in some embodiments edge 51 can follow an arcuate path, and/or can comprise gradual curves rather than right angle corners, as can any of the other exemplary oleophilic wetting features 50 (e.g., rib 53, groove, 55, gap 57, etc.) disclosed later herein. Edge 51 can be generally vertically oriented as in FIG. 5; or, can be somewhat angled away from vertical. Fluorinated barrier coating 200 may laterally continue underneath some or all of layer 52 (as in the exemplary embodiment of FIGS. 3-5), or may terminate e.g. in lateral proximity to edge 51.

Figure 6:
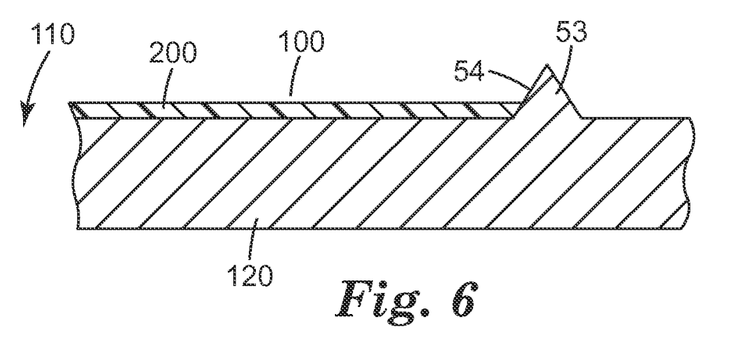
FIG. 6 is a partial cross sectional view of an exemplary microvolume oil acquisition basin comprising another exemplary oleophilic wetting feature.

FIG. 6 shows another exemplary design in which oleophilic wetting feature comprises oleophilic rib 53 that laterally bounds capacitive sensing element 110. Rib 53 comprises at least one face (e.g., face 54) that is nonfluorinated with a surface energy of greater than 30 dyne/cm. Fluorinated coating 200 may laterally terminate at rib 53 (as shown in FIG. 6) or may be present at least at some locations laterally outward of rib 53. Although shown in FIG. 6 as generally triangular in cross section, any suitable shape may be chosen, including square (e.g. with a generally flat top), rounded, and so on. Although shown as generally flat in FIG. 6, the at least one nonfluorinated face of rib 53 may have a secondary structure or texture (e.g., jagged, sinusoidal, pyramidal, moguled, scalloped, etc.), as can the nonfluorinated surface of any of the other exemplary oleophilic wetting features 50 disclosed herein. Rib 53 may be formed by any suitable method, e.g. by depositing material upon substrate 120. Rib 53 may be formed e.g. prior to deposition of fluorinated barrier coating 200; or, rib 53 may be formed after the deposition of coating 200. Those of ordinary skill will appreciate that there may be no firm dividing line between oleophilic wetting features 50 of the type of rib 53 and those of the type of edge 51 of layer 52.

Figure 7:
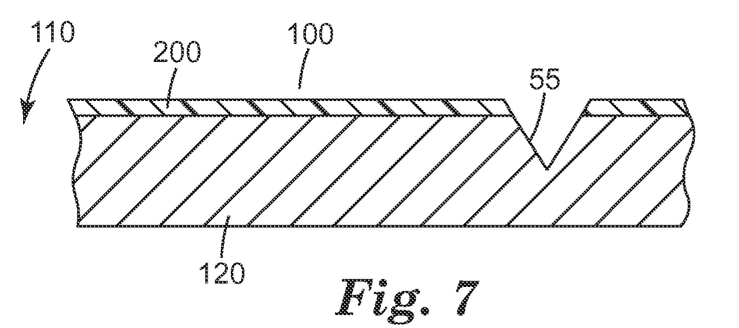
FIG. 7 is a partial cross sectional view of an exemplary microvolume oil acquisition basin comprising another exemplary oleophilic wetting feature.

FIG. 7 shows another exemplary design in which oleophilic wetting feature 50 comprises oleophilic groove 55 that laterally bounds capacitive sensing element 110. Groove 55 comprises at least one face that is nonfluorinated with a surface energy of greater than 30 dyne/cm. Fluorinated coating 200 may be present at least at some locations laterally outward of groove 55 (as shown in FIG. 7) or may terminate at groove 55. Although shown in FIG. 7 as generally triangular in cross section, any suitable shape may be chosen. Groove 55 may penetrate partially into substrate 120, as shown in FIG. 7. Groove 55 may be formed by any suitable method before or after the deposition of fluorinated barrier coating 200. For example, a tool may be traversed along the upper surface of substrate 120, removing any existing fluorinated barrier coating 200 and at least a portion of substrate 120, to provide a groove 55 of the general type shown in FIG. 7.

Figure 8:
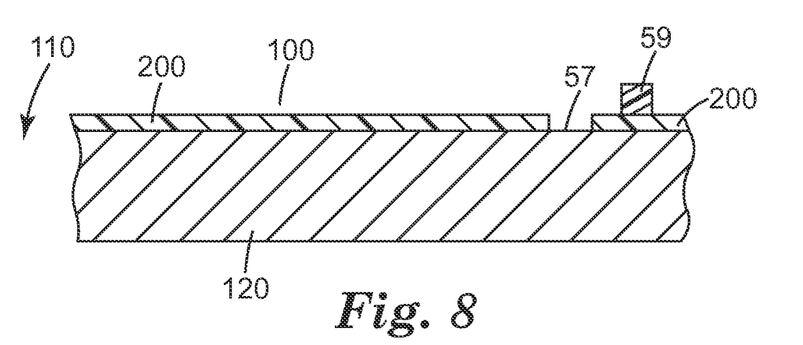
FIG. 8 is a partial cross sectional view of an exemplary microvolume oil acquisition basin comprising another exemplary oleophilic wetting feature.

FIG. 8 shows still another exemplary design in which oleophilic wetting feature 50 comprises oleophilic gap 57 in fluorinated barrier coating 200 at the desired location on substrate 120. Gap 57 may be provided by removing a portion of a previously deposited coating 200; or masking can be provided in the desired location during the forming (e.g. depositing) of fluorinated barrier coating 200 such that no fluorinated barrier coating is formed in the location designated to comprise gap 57. Gap 57 thus may comprise e.g. an exposed upper surface of substrate 120 or of a layer thereupon, as long as the exposed surface is nonfluorinated with a surface energy of greater than 30 dynes/cm. Fluorinated coating 200 may be present at least at some locations laterally outward of gap 57 (as shown in FIG. 8) or may terminate at gap 57. Those of ordinary skill will appreciate that there may be no firm dividing line between oleophilic wetting features 50 of the type of gap 57 and those of the type of groove 55.

Many variations and combinations of the above designs are possible. A single type of oleophilic wetting feature 50 can laterally bound all sides of capacitive sensing element 110; or a certain type (e.g., edge 51 of layer 52) can be positioned laterally outward of one portion of capacitive sensing element 110, and a different type (e.g., groove 55) can be positioned laterally outward of another portion of element 110, with the different types of wetting features combining to collectively laterally bound element 110. Although shown as generally continuous in the exemplary embodiments depicted herein, those of ordinary skill will appreciate that any oleophilic wetting feature 50 can comprise an interrupted or discontinuous design. That is, a strip, rib, groove, etc. may be collectively provided by a plurality of individual strip, rib or groove members, e.g. a plurality of suitably spaced and designed posts, rib segments, divots, gaps (in fluorinated barrier coating 200), and so on, rather than being a generally continuous edge, rib, groove, gap, etc.

In some embodiments a secondary stop feature 59 that laterally bounds oleophilic wetting feature 50 may be provided in order to prevent oil from penetrating laterally outward beyond oleophilic wetting feature 50 beyond a desired extent. Although shown in exemplary manner in combination with gap 57 (in FIG. 8), such a secondary stop feature 59 may be used with any oleophilic wetting feature 50, whether the wetting feature be an edge, rib, groove, etc. Secondary stop feature 59 may minimize or stop the flow of oil by providing a physical barrier, by virtue of having a suitable surface energy, or by a combination of both, and can be formed in any suitable manner of any suitable material. In some embodiments secondary stop feature 59 may be at least a portion of a sidewall that defines the lateral dimensions of basin 100.

Figure 9:
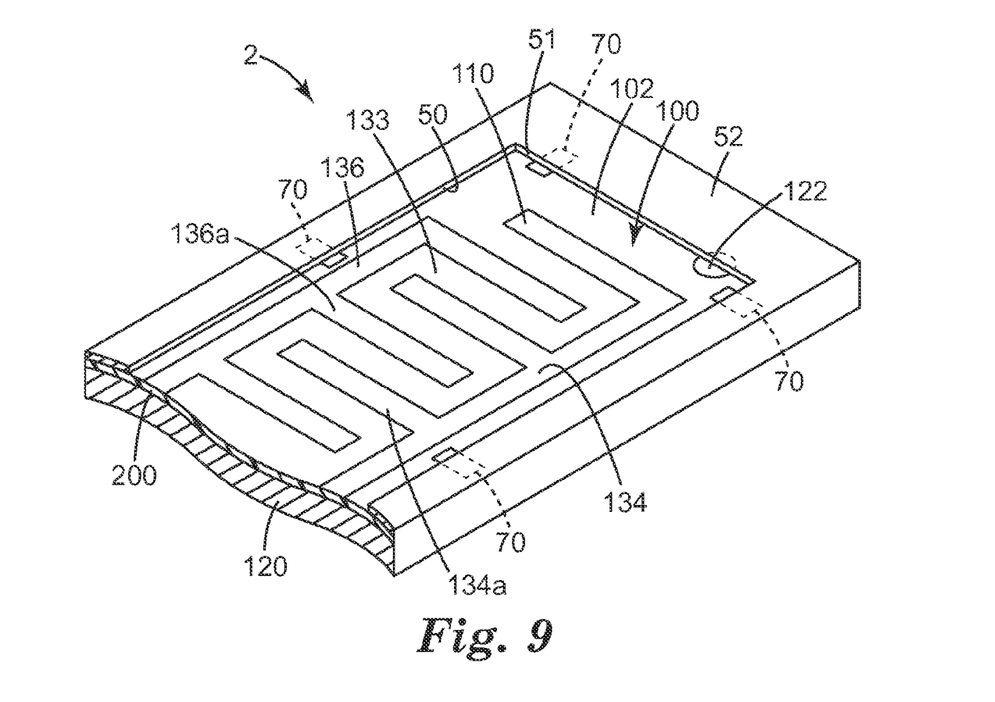
FIG. 9 is a perspective view of an exemplary microvolume oil acquisition basin comprising a capacitive sensing element with a fluorinated barrier coating and further comprising liquid sensors positioned proximate the perimeter of the basin.

As shown in exemplary manner in FIG. 9, in some embodiments, one or more fluid detection sensors 70 may be provided proximate oleophilic wetting feature 50. Such sensors may allow confirmation that liquid oil is present at least at or near a particular location within basin 100. Several such sensors may be spaced (whether uniformly or variably) along the length of oleophilic wetting feature 50, if desired. The sensors may extend laterally inward at least slightly (e.g., a few mm) into the area laterally bounded by oleophilic wetting feature 50, as shown in the exemplary embodiment of FIG. 9. Such a sensor or sensors may be e.g. a capacitive sensor that responds merely to the presence or absence of liquid oil (as opposed to capacitive sensing element 110 which should be capable of distinguishing changes in capacitance resulting from Total Polar Content of an oil sample). Such sensors might be formed on substrate 120 in the same operation as the formation of capacitive sensing element 110 (e.g., by deposition or formation of conductive traces); or, they may be provided separately. Any other suitable type of fluid detection sensor (e.g., optical sensors) may be used if desired.

Figure 10:
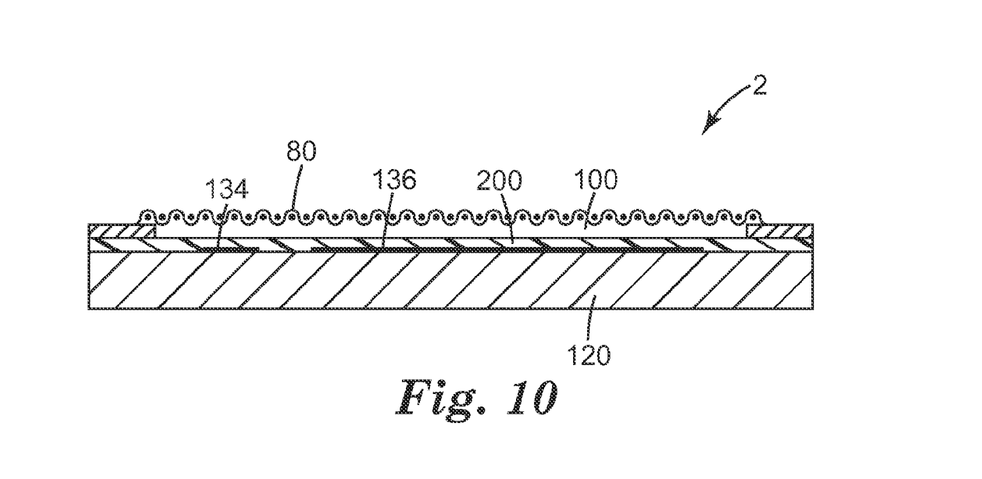
FIG. 10 is a cross sectional view of an exemplary microvolume oil acquisition basin comprising a capacitive sensing element with a fluorinated barrier coating and further comprising an oil-spreading sheet positioned over the basin.

As shown in exemplary manner in FIG. 10, in some embodiments an oil-spreading sheet 80 may be provided that is positioned upwardly adjacent capacitive sensing element 110 and is in overlapping relation with the entirety of capacitive sensing element 110. A slight vertical gap (e.g., between about 20 microns and about 500 microns in height) may be provided between the lower surface of sheet 80 and fluorinated barrier coating 200 (sheet 80 may however be in contact with a portion of oleophilic wetting feature 50). Sheet 80 may be sufficiently permeable to oil to allow an oil sample to interstitially penetrate through sheet 80 into basin 100 upon immersion of sample acquisition probe 2 into an oil supply. Instead, or in addition, one or more through-openings may be provided in sheet 80, and/or adjacent to sheet 80, to allow oil to reach into basin 100. Sheet 80 may act to assist in the spreading of the oil over the entirety of capacitive sensing element 110 (e.g., throughout basin 100) and in the maintaining of the oil in position over the entirety of capacitive sensing element 110 without dewetting. By definition, oil-spreading sheet 80 as used with sample acquisition probe 2 herein is distinguished from conventional filters (e.g. filtration membranes), absorbent pads and the like, by way of not being made of any organic polymeric or cellulosic material, by way of being able to withstand the temperatures experienced upon direct immersion of probe 2 into a (hot) oil supply, and by way of not performing any filtration function other than possibly blocking of gross particles e.g. of greater than 0.1 mm or more in size). Suitable materials for sheet 80 may include e.g. stainless steel mesh and the like. In various embodiments, oil-spreading sheet 80 may be used in conjunction with, or instead of, any of the exemplary oleophilic wetting features 50 described above. In the latter case, at least the portion of oil-spreading sheet 80 that laterally bounds capacitive sensing element 110 can in this context be considered to be an oleophilic wetting feature as disclosed herein.

In some embodiments, sample acquisition probe 2 does not comprise a compensating capacitor that is of similar design to capacitive sensing element 110 but does not contact an oil sample (i.e., that is provided on the lower side of substrate 120). In some embodiments, sample acquisition probe 2 does not comprise shielding designed to prevent capacitive sensing element 110 from responding to straying capacitances (e.g., from a metal wall of an oil supply container), since, as discussed later herein, device 1 as used herein may not be susceptible to such straying capacitances.

In some embodiments (e.g., as shown in FIG. 1), sample acquisition probe 2 is physically connected to control unit 400 by connecting member 410, which may be elongated so that probe 2 can be immersed into an oil supply by an operator who is holding control unit 400, without necessitating that control unit 400 be held unacceptably close to the oil supply. In some embodiments, connecting member 410 may be flexible. In specific embodiments, connecting member 410 may be reversibly shapable (e.g., into a bent, arched or arcuate configuration, an S-shaped configuration, etc.) so as to allow probe 2 to be most easily immersed into a particular oil supply. Connecting member 410 may be self-maintaining, meaning that it can remain in a particular shaped configuration without assistance from an operator. In some embodiments, connecting member 410 may be reversibly extendable (e.g., from an initial non-extended configuration, e.g. a retracted coil-spring configuration) into an extended configuration. If desired, a secondary handle may be supplied somewhere along the length of connecting member 410 to facilitate such extending. If desired, at least the outer surface of connecting member 410 may be made of a material with relatively low thermal conductivity, as may the casing of control unit 400.

Sample acquisition probe 2 and/or capacitive sensing element 110 may be disposed after a single use if desired; however, as disclosed herein, it may be reusable and in at least some embodiments it may advantageously be used multiple times (e.g., five, ten, twenty, or more). Sample acquisition probe 2 and/or capacitive sensing element 110 may be detachable e.g. from connecting member 410 so that is may be replaced.

Sample acquisition probe 2 and capacitive sensing element 110 therein (as well as temperature sensor 122, and liquid sensor(s) 70, if present) are operatively connected to control unit 400 by any suitable mechanism. In some embodiments, this may be achieved by conductive wires and/or fiber optic cables running through connecting member 410. In other embodiments, this may be achieved by wireless communication between probe 2 and control unit 400 (e.g., by a Bluetooth connection or the like). In such embodiments, it may not be required that probe 2 be physically connected to control unit 400 (e.g., probe 2 may merely have a handle that allows probe 2 to be immersed in an oil supply). However, wireless communication between probe 2 and control unit 400 may be used even if the two are physically connected by connecting member 410.

According to methods disclosed herein a microvolume oil sample may be acquired into a microvolume oil acquisition basin of an oil acquisition probe and a capacitance property measured thereof by way of a capacitive sensing element within the oil acquisition basin. (Although described herein for convenience in the context of probe 2 comprising oleophilic wetting feature 50, it is noted that the sample acquisition and measurement methods disclosed herein do not necessarily require the presence of oleophilic wetting feature 50). An oil sample may be acquired from any oil supply (e.g., oil vat) which may be at any suitable temperature including elevated temperatures such as typically used in fry-cooking Sample acquisition probe 2 may be at least partially immersed into the oil supply to a sufficient extent to allow a microvolume oil sample to be acquired into microvolume oil acquisition basin 100. As defined herein, the terms acquire, acquisition, etc., are limited to ingress of oil into basin 100 by way of basin 100 being at least partially immersed in an oil supply a sample of which then enters basin 100 without further manipulation or action by an operator. Such terms do not encompass the act of depositing, transferring, or otherwise inserting into basin 100, an oil sample which has been previously removed from an oil supply.

Basin 100 may have lateral dimensions defined by walls (e.g., sidewalls). Such sidewalls may be the same as oleophilic wetting feature 50 (e.g., as in the exemplary embodiment of FIGS. 2 and 3) Or the sidewalls may be different from oleophilic wetting feature 50 and may be laterally outward therefrom (e.g., so as to laterally bound oleophilic wetting feature 50). In various embodiments, lateral dimensions of basin 100 may range from, e.g., about 0.5 cm to about 6 cm in (noting that basin 100 may be any suitable lateral shape, e.g., square, rectangular, round, irregular, etc.), with basin 100 thus comprising in various embodiments an area of from about 1 square centimeter to about 20 square centimeters. In various embodiments, basin 100 may have a depth in the range of at least 10, 20, or 40 microns. In further embodiments, basin 100 may have a depth of at most 1000, 500, or 200 microns. By whatever combination of depth and lateral dimensions, microvolume oil acquisition basin 100 by definition has a nominal capacity of no more than 500 microliters. In this context nominal capacity means the volume of basin 100 as bounded by a plane that is even with the uppermost edge of the sidewalls that define the lateral dimensions of basin 100 (noting that in actual use a portion of an oil sample may bulge upward slightly beyond this plane, e.g. due to surface energy effects). In various embodiments, microvolume oil acquisition basin 100 has a nominal capacity of less than about 100 microliters, less than about 50 microliters, or less than about 20 microliters. It should be noted that the volume of oil acquired may not equal the nominal capacity of basin 100. That is, in some cases an acquired oil sample may not fill basin 100 to the full depth of basin 100. This may be acceptable, or even advantageous, e.g. as long as the oil sample is sufficiently motivated by the oleophilic wetting feature to cover the entirety of capacitive sensing element 110. And, as mentioned above, in some cases the actual volume of oil may slightly exceed the nominal capacity of basin 100.

Sample acquisition probe 2 may be at least partially immersed into the oil supply at any suitable angle (relative to the surface of the oil supply), e.g., between about 20 degrees and 80 degrees; such that a microvolume oil sample is acquired within basin 100 and does not run or leak out of basin 100 upon removal of probe 2 from the oil supply. Probe 2 may then be removed from the oil supply, whereupon any excess oil may be removed from probe 2, leaving only the acquired microvolume oil sample within basin 100 and potentially a small amount of residual oil on other surfaces of probe 2 and/or connecting member 410. Any excess oil may be removed from probe 2 passively or actively. That is, the action of gravity alone may remove any excess oil from probe 2 and leave behind the acquired microvolume oil sample in basin 100 (e.g., by positioning probe 2 e.g. such that any excess oil runs off under the influence of gravity). Or, a tool (e.g., blade, swab, etc.) may be actively used to squeegee off, blot away, etc. any excess oil.

After removal of sample acquisition probe 2 from the oil supply, capacitive sensing element 110 of sample acquisition probe 2 can be used to measure a capacitive property of the microvolume oil sample in oil acquisition basin 100. This measurement may be able to be performed almost immediately, e.g. within 10 seconds, 5 seconds, 2 seconds, or less, from the time at which probe 2 is removed from the oil supply. A single capacitive measurement may be performed; or, multiple measurements may be taken e.g. and averaged together if desired. During the measuring of the capacitive property, the temperature of the acquired microvolume oil sample may be less (e.g., more than 2, 5, 10, or 20° C. less) than the temperature of the oil in the oil supply (since probe 2 and the oil sample therein may have cooled off at least somewhat, e.g. at least a few degrees C., during the time since their removal from the oil supply). It may not be necessary to wait for the temperature of the acquired microvolume oil sample to come to an equilibrium state to make the capacitive measurement(s). In fact, dynamic measurement may be performed (meaning that the temperature of the oil is dropping at a rate of at least 5 degrees C. per minute during the measurement of the capacitive property). As long as the temperature of the acquired microvolume oil sample is measured with sufficient accuracy (e.g. by aforementioned temperature sensor 122) during the capacitive measurement so that the measured capacitive property of the microvolume oil sample can be compensated for the temperature of the oil, there may be no need to wait until the oil sample has come to an equilibrium temperature before performing the measurement, thus a dynamic measurement may be performed.

In some embodiments the capacitive measurement(s) can be performed with the temperature of the acquired microvolume oil sample uncontrolled, meaning that no active temperature control element (i.e., a powered heating element of any type) is operative to control the temperature of the microvolume oil sample and/or probe 2 during the interval between acquiring the oil sample and measuring the capacitance thereof, or during the measuring itself. However, in some embodiments, the temperature may be controlled e.g. by use of a powered heating element, if desired.

Those of ordinary skill will appreciate that upon immersion of sample acquisition probe 2 into a supply of oil (i.e., hot oil) probe 2 may heat up at least to some extent. After acquisition of a microvolume oil sample into basin 100 and removal of probe 2 from the oil supply, probe 2 will begin to cool back down (e.g., when held in air). The acquired microvolume oil sample will also begin to cool down upon its removal from the oil supply, as mentioned above. (At some point the microvolume oil sample may thermally equilibrate with probe 2 such that they are both at similar or the same temperatures, after which they may both cool together). As mentioned, a capacitive measurement may be performed while the temperature of the acquired oil sample and/or probe 2 are still changing. It may thus be desirable to design probe 2 so as to optimize this procedure. For example, it may be desirable to configure probe 2 and the method of use thereof so that the temperature of the acquired oil sample and that of probe 2 closely approach each other before the capacitive measurement is made (e.g., in order that the most accurate temperature measurement of the oil sample is made so that appropriate compensation can be made most accurately). Accordingly, probe 2 may comprise a thermal mass element 121 as shown in exemplary manner in FIG. 2. Thermal mass element 121 is passive and is not powered in any manner and thus may be distinguished e.g. from an active temperature control element. Element 121 may be designed of suitable size, and may be made of materials with suitable heat capacity, thermal conductivity, etc., to allow the herein-disclosed dynamic (and, optionally, temperature-uncontrolled) measurements to be satisfactorily made. That is, a suitable passive thermal mass element may act in combination with the other components of probe 2 (e.g., substrate 120) to govern or limit the rate at which probe 2 heats up upon immersion in a hot oil supply, and/or to govern and/or limit the rate at which probe 2 and/or an acquired microvolume oil sample contained in basin 100 therein, cool off upon removal of probe 2 from the oil supply. For example, thermal mass element 121 may increase the thermal mass of probe 2 such that probe 2 cools off sufficiently slowly that the acquired microvolume oil sample relatively quickly thermally equilibrates to the temperature of probe 2 while probe 2 is still at a relatively high temperature. Further, thermal mass element 121 may limit the rate of cooling of probe 2 with a microvolume oil sample thermally equilibrated thereto, such that a dynamic and/or temperature-uncontrolled capacitive measurement can be optimally obtained. Thermal mass element 121 may be made of any suitable material, e.g. a metal such as stainless steel, and may be attached to substrate 120 e.g. by a thermally conductive adhesive or by any other attachment mechanism that allows suitable thermal communication between thermal mass element 121 and substrate 120.

In performing the methods disclosed herein, basin 100 may, but does not have to, comprise oleophilic wetting feature 50, and/or liquid sensor(s) 70, and/or oil-spreading sheet 80. If oil-spreading sheet 80 is used, oil may penetrate directly through the interstices of sheet 80 to reach the interior of basin 100; or, one or more small openings or through-penetrations may be provided either within the body of sheet 80, or laterally outward therefrom, in order to enhance the ability of oil to penetrate into basin 100.

The disclosed methods have significant advantages in that they may not require more than a momentary immersion (e.g., less than about 5 seconds, 2 seconds, or 1 second) of probe 2 into an oil supply to acquire and remove a sample (in contrast to methods which require a probe to be held in an oil supply for a considerable length of time, e.g. 20 seconds or more, while measurements are taken). And, it may not be necessary that an oil sample be acquired from a particular location in the oil supply (e.g., more than a certain distance from a wall of the oil supply container), as is often necessary with systems that measure capacitance of the oil with a probe while the probe is immersed in the oil supply. Further, it may not require that an acquired sample be transported to a secondary device to perform the actual capacitance measurement. And, as mentioned, it may not require a long waiting period for an acquired oil sample to come to thermal equilibrium, and it may not require the temperature of the acquired oil sample to be controlled. Still further, the use of microvolume basin 100 may enable multiple measurements to be made (whether repeat measurements of a single oil supply, or measurements of different oil supplies) without requiring that basin 100 be cleaned between measurements. That is, basin 100 may have an auto-cleaning capability, meaning that when probe 2 with basin 100 containing a previously acquired microvolume oil sample is immersed into an oil supply, the previously acquired microvolume oil sample may be liberated (e.g., physically dislodged, dissolved, etc.) from the basin and replaced by oil from the current oil supply. In the particular case of successive measurements of different oil supplies, the microvolume sample will typically be so small in comparison to the oil supply that any previously-acquired sample is diluted amongst the next-measured oil supply that it does not unacceptably compromise the accuracy of the measuring of the capacitance of the second oil supply. If desired, however, an oil sample may be removed from basin 100 (e.g., by wiping or blotting with an absorbent material) between measurements, and/or at the conclusion of a series of measurements.

Fluorinated barrier coating 200 will now be discussed (although the term coating is used for convenience, it should be understood to encompass any layer containing a fluorinated material as described herein, regardless of the particular method of deposition). Fluorinated barrier coating 200 can be comprised of any fluorinated material that comprises sufficient oil and water repellency, oil and water barrier properties, mechanical strength and integrity, and durability, to provide the above-discussed advantages, while not unacceptably affecting the measuring of capacitance. In various embodiments, fluorinated barrier coating 200 may comprise a surface energy of less than 30 dynes/cm, less than about 25 dynes/cm, less than about 20 dynes/cm, or less than about 15 dynes/cm. In certain embodiments, fluorinated barrier coating 200 comprises a surface energy of from about 10 dynes/cm to about 30 dynes/cm. Fluorinated barrier coating 200 may comprise a thickness of at least about 0.10 microns, at least about 0.2 microns, at least about 0.5 microns, or at least about 1.0 microns. In further embodiments, the thickness of fluorinated barrier coating 200 may be at most about 12 microns, at most about 8 microns, or at most about 4 microns. Fluorinated barrier coating 200 may comprise a total fluorine content of at least 0.05 percent by weight. By total fluorine content is meant the amount of fluorine in relation to the entire (dry, e.g. after removal of any coating solvent) composition of the coating. In various embodiments, the total fluorine content may be at least about 0.5 percent, at least about 5.0 percent, or at least about 20 percent, by weight. In various embodiments, fluorinated barrier coating 200 may comprise a crosslinked material as discussed below.

Fluorinated barrier coating 200 may be obtained from the reaction product of at least one fluorinated unsaturated compound (that may, e.g., polymerize by a free-radical mechanism). In some embodiments, coating 200 may comprise the reaction product of molecules that comprise, in the same molecule, fluorine atoms (e.g., in $CF_3$ groups, larger fluorinated alkyl groups, and the like) and acrylate and/or methacrylate groups (such molecules will be referred to herein as fluorinated/(meth)acrylate molecules). In various embodiments, the fluorinated groups may comprise terminal groups, pendant groups, side-chain groups, and the like; or they may comprise segments (e.g., backbone segments) located in between two or more terminal (meth)acrylate groups. In some embodiments the reaction product may be only of fluorinated/(meth)acrylate molecules with fluorinated/(meth)acrylate molecules. However, in some cases it may only be necessary to include an amount of fluorinated/(meth)acrylate molecules (and/or a level of fluorine atoms in such molecules) to provide the above-listed advantages. Thus in some embodiments, the reaction product may be of fluorinated/(meth) acrylate molecules with (meth)acrylate molecules that are not fluorinated.

Fluorinated barrier coating 200 may be obtained by depositing a composition (referred to herein for convenience as a coating composition although this is not meant to limit the method of deposition to coating) onto substrate 120 bearing electrodes 134 and 136 thereon. Such coating compositions may comprise e.g. fillers such as inorganic particles, nanoparticles, etc., if such fillers impart desirable properties (e.g., durability and the like), and may further comprise additives, initiators, crosslinking agents (which may be fluorinated or nonfluorinated), coupling agents, stabilizers, and the like as is well known in the art.

Coatings thus formed by such reaction products will typically comprise at least linear high molecular weight fluorinated materials (after being reacted). If the molecules used are multifunctional (e.g., comprising more than one (meth) acrylate group), the coating may comprise a network rather than substantially linear polymer chains. Often, the reaction product will comprise fluorine atoms bonded to substituents of the chain backbones (e.g., in the case of (meth)acrylate molecules in which fluorine atoms are typically not found directly bonded to the reactive C=C bond).

In particular embodiments, at least some of the fluorinated/ (meth)acrylate molecules comprise perfluoropolyether (meth)acrylate molecules. As used herein "perfluoropolyether (meth)acryl molecule" refers to a molecule comprising at least one perfluoropolyether group and at least one (meth) acryl group typically joined by a linking group. Perfluoropolyether (meth)acryl molecules can be represented by the following Formula I:

$$(R_f)—[(W)—(R_A)]_w \qquad \text{(Formula I)}$$

wherein $R_f$ is perfluoropolyether group; W is a linking group; and $R_A$ is a (meth)acryl group or —COCF=CH$_2$; and w is 1 or 2.

The perfluoropolyether group $R_f$ can be linear, branched, cyclic, or combinations thereof and can be saturated or unsaturated. The perfluoropolyether has at least two catenated oxygen heteroatoms. Exemplary perfluoropolyethers include, but are not limited to, those that have perfluorinated repeating units selected from the group of —(C$_p$F$_{2p}$)—, —(C$_p$F$_{2p}$O)—, —(CF(Z))—, —(CF(Z)O)—, —(CF(Z)C$_p$F$_{2p}$O)—, —(C$_p$F$_{2p}$CF(Z)O)—, —(CF$_2$CF(Z)O)—, or combinations thereof. In these repeating units, p is typically an integer of 1 to 10. In some embodiments, p is an integer of 1 to 8, 1 to 6, 1 to 4, or 1 to 3. The group Z is a perfluoroalkyl group, perfluoroether group, perfluoropolyether, or a perfluoroalkoxy group, all of which can be linear, branched, or cyclic. The Z group typically has no more than 12 carbon atoms, no more than 10 carbon atoms, or no more than 9 carbon atoms, no more than 4 carbon atoms, no more than 3 carbon atoms, no more than 2 carbon atoms, or no more than 1 carbon atom. In some embodiments, the Z group can have no more than 4, no more than 3, no more than 2, no more than 1, or no oxygen atoms. In these perfluoropolyether structures, the different repeat units can be distributed randomly along the chain.

$R_f$ can be monovalent or divalent. In some molecules where $R_f$ is monovalent, the terminal groups can be (C$_p$F$_{2p+1}$)—, (C$_p$F$_{2p+1}$O)—, (X'C$_p$F$_{2p}$O)—, or (X'C$_p$F$_{2p+1}$)— where X' is hydrogen, chlorine, or bromine and p is an integer of 1 to 10. In some embodiments of monovalent $R_f$ groups, the terminal group is perfluorinated and p is an integer of 1 to 10, 1 to 8, 1 to 6, 1 to 4, or 1 to 3. Exemplary monovalent $R_f$ groups include CF$_3$O(C$_2$F$_4$O)$_n$CF$_2$—, and C$_3$F$_7$O(CF(CF$_3$)CF$_2$O)$_n$CF (CF$_3$)— wherein n has an average value of 0 to 50, 1 to 50, 3 to 30, 3 to 15, or 3 to 10.

Suitable structures for divalent $R_f$ groups include, but are not limited to, —CF$_2$O(CF$_2$O)$_q$(C$_2$F$_4$O)$_n$CF$_2$—, —(CF$_2$)$_3$O (C$_4$F$_8$O)$_n$(CF$_2$)$_3$—, —CF$_2$O(C$_2$F$_4$O)$_n$CF$_2$—, and —CF (CF$_3$)(OCF$_2$CF(CF$_3$))$_s$OC$_t$F$_{2t}$O(CF(CF$_3$)CF$_2$O)$_n$CF (CF$_3$)—, wherein q has an average value of 0 to 50, 1 to 50, 3 to 30, 3 to 15, or 3 to 10; n has an average value of 0 to 50, 3 to 30, 3 to 15, or 3 to 10; s has an average value of 0 to 50, 1 to 50, 3 to 30, 3 to 15, or 3 to 10; the sum (n+s) has an average value of 0 to 50 or 4 to 40; the sum (q+n) is greater than 0; and t is an integer of 2 to 6.

As synthesized, molecules according to Formula I may include a mixture of $R_f$ groups. The average structure is the structure averaged over the mixture components. The values of q, n, and s in these average structures can vary, as long as the compound has a number average molecular weight of at least about 400. Compounds of Formula I often have a molecular weight (number average) of 400 to 5000, 800 to 4000, or 1000 to 3000.

The linking group W between the perfluoropolyether segment and (meth)acryl or —COCF=CH$_2$ endgroup may include a divalent group selected from an alkylene, arylene, heteroalkylene, or combinations thereof and an optional divalent group selected from carbonyl, carbonyloxy, carbonylimino, sulfonamido, or combinations thereof. W can be unsubstituted or substituted with an alkyl, aryl, halo, or combinations thereof. The W group typically has no more than 30 carbon atoms. In some compounds, the W group has no more than 20 carbon atoms, no more than 10 carbon atoms, no more than 6 carbon atoms, or no more than 4 carbon atoms. For example, W can be an alkylene, an alkylene substituted with an aryl group, or an alkylene in combination with an arylene.

In further embodiments, at least some of the fluorinated/ (meth)acrylate molecules comprise perfluoropolyether urethane (meth)acrylate molecules. Such molecules may be made for example by first reacting a polyisocyanate with a perfluoropolyether molecule (e.g., of the type described above) containing an alcohol, thiol, or amine group. The perfluoropolyether urethane additive may then be combined with a (e.g. non-fluorinated) isocyanate reactive multifunctional free-radically polymerizable (meth)acrylate crosslinker. Other methods are possible as is known in the art.

An exemplary perfluoropolyether urethane (meth)acrylate molecules is shown as follows:

(Formula 2)

In the above, "HFPO" represents a perfluoropolyether as described in further detail in PCT Published Application WO 2009/029438 to Pokorney et al. This document describes perfluoropolyether urethane (meth)acrylate molecules, the preparation thereof, and the preparation of coating compositions and reaction products thereof, and is incorporated by reference herein for this purpose.

The perfluoropolyether urethane (meth)acrylate materials described herein may be the only fluorinated material employed in the coating composition, or may be used in combination with various other fluorinated materials having at least one moiety selected from fluoropolyether, fluoroalkyl, and fluoroalkylene linked to at least one free-radically reactive group (e.g., a (meth)acrylate group). When such a second fluorinated material employed, it may be preferred that such second fluorinated compound also comprises an HFPO—moiety.

In the above embodiments, the (meth)acrylate molecules (whether fluorinated or not) can be monofunctional (i.e., bearing a single (meth)acrylate group), or multifunctional (i.e. bearing two or more (meth)acrylate groups). The term (meth)acrylate means a molecule that comprises at least one acrylate group and/or at least one methacrylate group. In describing these materials, the term "compound" means a collection of molecules of the described type.

In summary, in some embodiments fluorinated barrier coating 200 may be made by the reaction of any suitable reactive compounds that comprise fluorine atoms. Such fluorine atoms may be present in fluorinated alkyl groups (that are, e.g., pendant groups of a reactive monomer or oligomer). Such groups might include e.g. $CF_3$, $C_2F_5$, $C_3F_7$, $C_4F_9$, $C_5F_{11}$, $C_6F_{13}$, $C_7F_{15}$, $C_8F_{17}$, as well as the above-described perfluoropolyethers and the like. In other embodiments, fluorinated barrier coating may be made by the deposition of fluorinated polymeric materials, as well as by other methods. Such formation methods, as well as additional details of above-discussed fluorinated compositions and methods of making, are described in U.S. patent application Ser. No. 12/542,829 to Yu et al., titled Capacitive Oil Quality Monitoring Sensor with Fluorinated Barrier Coating, which is incorporated by reference herein in its entirety.

It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention. Thus, the scope of the present invention should not be limited to the specific illustrative structures described herein, but rather by the structures described by the language of the claims, and the equivalents of those structures. To the extent that there is a conflict or discrepancy between this specification and the disclosure in any document incorporated by reference herein, this specification will control.

What is claimed is:

1. A device for acquiring a microvolume oil sample from a supply of cooking oil and for measuring a capacitive property of the microvolume oil sample, comprising:
   a cooking oil sample acquisition probe comprising a microvolume oil acquisition basin with a capacitive sensing element located on the floor of the basin and with a fluorinated barrier coating located atop the basin floor and the capacitive sensing element thereon; and
   wherein the capacitive sensing element and the fluorinated barrier coating atop the capacitive sensing element are laterally bounded by an oleophilic wetting feature.

2. The device of claim 1 wherein the oleophilic wetting feature comprises a laterally-inward facing exposed edge of a layer of oleophilic material that protrudes vertically above the fluorinated barrier coating in an area laterally bounding the basin.

3. The device of claim 1 wherein the capacitive sensing element is provided on a substrate, and wherein the oleophilic wetting feature comprises a groove that penetrates partially into the substrate with the groove comprising at least one surface that does not comprise a fluorinated barrier coating.

4. The device of claim 1 wherein the oleophilic wetting feature comprises a rib that protrudes upwardly above the fluorinated coating with the rib comprising at least one surface that does not comprise a fluorinated barrier coating.

5. The device of claim 1 wherein the oleophilic wetting feature comprises an oleophilic exposed upper surface of a substrate upon which the capacitive sensing element is provided, or an oleophilic exposed upper surface of a layer present upon the substrate, in an area of the substrate or layer thereon in which a fluorinated barrier coating is not present.

6. The device of claim 1 further comprising a secondary stop feature that laterally bounds the oleophilic wetting feature and that prevents the oil from penetrating laterally outward beyond the secondary stop feature.

7. The device of claim 1, further comprising at least one liquid sensor proximate the oleophilic wetting feature.

8. The device of claim 7, wherein a plurality of liquid sensors are spaced along at least a portion of a length of the oleophilic wetting feature.

9. The device of claim 1, wherein the cooking oil sample acquisition probe does not comprise an active temperature control element.

10. The device of claim 1, wherein the capacitive sensing element is provided on a substrate and wherein the cooking oil sample acquisition probe comprises a passive thermal mass element that is located adjacent a lower surface of at least a portion of the substrate and that is in thermal contact with the substrate or with a layer of material that is in thermal contact with the substrate.

11. The device of claim 1, wherein the cooking oil sample acquisition probe comprises an oil-spreading sheet that is positioned upwardly adjacent the capacitive sensing element and is in overlapping relation with the entirety of the capacitive sensing element.

12. The device of claim 11 wherein the oil-spreading sheet is comprised of a metal mesh.

13. The device of claim 1, wherein the cooking oil sample acquisition probe is physically connected to a control unit by an elongated connecting member.

14. The device of claim 13, wherein the connecting member is flexible and is reversibly shapeable into different self-maintaining configurations.

15. The device of claim 13 wherein the connecting member is reversibly extendable from a non-extended configuration into an extended configuration.

16. The device of claim 1, wherein the cooking oil sample acquisition probe is operatively connected to a control unit by wireless communication.

17. A method of measuring a capacitive property of a microvolume oil sample, comprising:
   providing a capacitive sensing element located on the floor of a microvolume oil acquisition basin of a cooking oil sample acquisition probe, wherein the probe comprises a fluorinated barrier coating located atop the basin floor and the capacitive sensing element thereon, and wherein the capacitive sensing element and the fluorinated barrier coating atop the capacitive sensing element are laterally bounded by an oleophilic wetting feature;
   immersing the cooking oil sample acquisition probe at least partially into a supply of cooking oil and withdrawing the probe from the supply of cooking oil such that a microvolume oil sample is retained within the oil acquisition basin in such manner as to completely cover the capacitive sensing element; and
   using the capacitive sensing element to measure a capacitive property of the microvolume oil sample.

18. The method of claim 17 wherein the capacitive property of the microvolume oil sample is measured while the temperature of the microvolume oil sample is less than the temperature of the oil in the supply of cooking oil.

19. The method of claim 18 wherein the capacitive property of the microvolume oil sample is measured dynamically while the temperature of the microvolume oil sample is dropping.

20. The method of claim 18 wherein the capacitive property of the microvolume oil sample is measured with the microvolume oil sample at an uncontrolled temperature.

21. The method of claim 18 wherein the cooking oil sample acquisition probe comprises a temperature sensor and wherein the temperature of the microvolume oil sample is measured during the measuring of the capacitive property of the microvolume oil sample.

22. The method of claim 17 comprising at least partially immersing the cooking oil sample acquisition probe into a first cooking oil supply, withdrawing the probe from the first cooking oil supply such that a first microvolume oil sample is retained within the oil acquisition basin, measuring a capacitive property of the first microvolume oil sample, and then immersing the cooking oil sample acquisition probe into a second cooking oil supply which may be the same or different from the first cooking oil supply, withdrawing the probe from the second cooking oil supply such that a second microvolume oil sample is retained within the oil acquisition basin, and measuring a capacitive property of the second microvolume oil sample, without cleaning the first microvolume oil sample out of the oil acquisition basin prior to immersing the probe into the second cooking oil supply.

23. The method of claim 17 wherein the cooking oil sample acquisition probe is at least partially immersed into the supply of cooking oil with the floor of the microvolume oil acquisition basin oriented at an angle of between 80 and 20 degrees relative to the surface of the supply of cooking oil.

24. The method of claim 17 wherein the cooking oil sample acquisition probe is at least partially immersed into the supply of cooking oil for a time of less than about less than about two seconds before being removed therefrom.

25. The method of claim 17 further comprising correlating the measured capacitive property of the microvolume oil sample with a Total Polar Content of the oil, and reporting an indication of oil quality based on the Total Polar Content of the oil.

26. The method of claim 17 wherein the cooking oil sample acquisition probe comprises at least one liquid sensor proximate the oleophilic wetting feature.

27. The method of claim 17 wherein the cooking oil sample acquisition probe comprises an oil-spreading sheet that is positioned upwardly adjacent the capacitive sensing element and is in overlapping relation with the entirety of the capacitive sensing element.

28. The method of claim 17 wherein the cooking oil sample acquisition probe is physically connected to a control unit by an elongated connecting member that is flexible and is reversibly shapeable into different self-maintaining configurations.

29. The method of claim 17, wherein the cooking oil sample acquisition probe is operatively connected to a control unit by wireless communication.

* * * * *

UNITED STATES PATENT AND TRADEMARK OFFICE
CERTIFICATE OF CORRECTION

Page 1 of 1

PATENT NO.        : 8,829,928 B2
APPLICATION NO.   : 13/227702
DATED             : September 9, 2014
INVENTOR(S)       : Bernard Gonzalez It is certified that error appears in the above-identified patent and that said Letters Patent is hereby corrected as shown below:

IN THE SPECIFICATION:

<u>Column 9</u>
Line 15, Delete "fry-cooking" and insert -- fry-cooking. --, therefor.

IN THE CLAIMS:

<u>Column 18</u>
Line 8, In Claim 24, after "time of" delete "less than about".

Signed and Sealed this
Tenth Day of February, 2015

Michelle K. Lee
*Deputy Director of the United States Patent and Trademark Office*